United States Patent [19]

Andersen et al.

[11] Patent Number: 4,528,268
[45] Date of Patent: Jul. 9, 1985

[54] APPARATUS AND METHOD FOR TESTING THE SUFFICIENCY OF STERILIZATION

[75] Inventors: Harold W. Andersen; Charles H. Harrison, both of Oyster Bay, N.Y.

[73] Assignee: H. W. Andersen Products Inc., Oyster Bay, N.Y.

[21] Appl. No.: 336,129

[22] Filed: Dec. 31, 1981

[51] Int. Cl.³ .......................... C12Q 1/22; C12M 1/24; B65D 25/08
[52] U.S. Cl. .................................... 435/31; 435/294; 435/296; 435/299; 435/300; 435/311; 435/810; 436/1; 436/807; 436/810; 206/219; 206/222; 215/227; 215/DIG. 8
[58] Field of Search ................. 435/31, 294, 296, 810, 435/311, 299, 300; 436/1, 807, 810; 206/219, 222; 215/227, DIG. 8

[56] References Cited

U.S. PATENT DOCUMENTS 3,440,144  4/1969  Anderson ........................... 435/31
4,304,869  12/1981  Dyke ................................. 435/31

Primary Examiner—Sam Rosen
Assistant Examiner—K. S. Moss
Attorney, Agent, or Firm—Jordan and Hamburg

[57] ABSTRACT

Apparatus and method for testing the sufficiency of sterilization includes a test tube having a distal end in which a bacterial spore element is disposed. A sealed glass ampule containing a sterile liquid culture medium is disposed in the test tube and a plunger having a fenestration closed with a hydrophobic filter is fitted slidingly in the open end of the test tube. In use, the apparatus is exposed to sterilization, and thereafter the plunger is pushed down into the test tube to engage the ampule to slide the latter into engagement with an ampule-engaging means to thereby fracture or break the ampule so that the contents of the ampule are released into the test tube to contact the spore element, whereby the apparatus is then subjected to incubation, the sufficiency of the sterilization being thereby determined.

21 Claims, 13 Drawing Figures

APPARATUS AND METHOD FOR TESTING THE SUFFICIENCY OF STERILIZATION

BACKGROUND OF THE INVENTION

This invention is related to U.S. Pat. No. 3,440,144 issued Apr. 22, 1969 and U.S. Pat. No. 3,476,506 issued Nov. 4, 1969, both of which are assigned to the present assignee, H. W. Andersen Products, Inc., of Oyster Bay, N.Y. and both of which are incorporated herein by reference as if fully set forth herein.

There are two types of controls generally available for determining the adequacy of hospital sterilization procedures. These are color change indicators and bacterial spore preparation. This invention relates to a bacterial spore test.

Most bacterial spore preparations for sterility testing are made in the form of small paper strips which contain a high concentration of live microorganisms. To correctly challenge a sterilization cycle, they must be placed in the least accessible places in the sterilization load. After the sterilization cycle has been completed, these paper control strips are transferred to a suitable sterile culture medium using standard accepted aseptic transfer techniques. If a sterilization process kills the highly resistant control bacterial spores (i.e. renders them incapable of reproduction when cultured), it is generally assumed that all other microorganisms present in the load have also been destroyed. Unfortunately, these spore strips are sometimes contaminated with live bacteria in the process of transferring them from the sterilization load to the tube of culture broth, yielding a false positive result (culture positive when load was actually sterile). Then the organism growing in the broth must be painstakingly identified to determine if it is the one planted or just a chance contaminant.

As a safety factor, these preparations are adjusted to contain a quantity of bacterial spores well above normal contamination limits. Bacterial spores vary in their resistance to different sterilizing agents and care must be taken in the choice of the proper species. *Bacillus subtilis* variant *niger* (*B. globigii*) spores are highly resistant to the lethal effects of ethylene oxide gas. Spore preparations containing these microorganisms in concentrations of 1,000,000 are commonly used as controls for ethylene oxide gas sterilization systems in every country in the western world.

Recently, German hygiene authorities have suggested an even higher standard of sterilizing efficiency. It is well recognized in the international scientific community that both suspension in a protein substrate, like blood serum, and desiccation make bacterial spores much more difficult to sterilize. The DIN Committee had proposed a test piece that consists of one million *Bacillus globigii* spores, suspended in a small amount of sheep's blood and vacuum dried at the bottom of a glass test tube stoppered with a highly compressed tissue paper stopper. It is expected that this test device, still tightly stoppered, will be exposed to the atmosphere of the sterilizer. At the end of the sterilization cycle, the test piece is removed and sent to the laboratory where a microbiologist must add the appropriate culture broth to the tube, taking meticulous care to exclude any chance bacterial contamination. If there is no growth of microorganisms in the tube after incubation, the test is said to demonstrate that the sterilizer did, in fact, reach sterilizing conditions during the cycle. If there is growth of microorganisms in the test tube, the sterilizer is considered to have failed to sterilize both the test piece and the instruments in that sterilizer load.

Unfortunately, the configuration of the aforementioned DIN test piece is not appropriate for all known sterilizing systems. For example, the aforementioned DIN test piece would be inappropriate for testing in a sterilization system currently marketed by H. W. Andersen Products, Inc. of Oyster Bay, N.Y., the present assignee, under the Registered Trademark "ANPROLENE" and as further set forth in the aforementioned U.S. Pat. No. 3,476,506 assigned to the present assignee H. W. Andersen Products, Inc. The aforementioned "ANPROLENE" system and the aforementioned U.S. Pat. No. 3,476,506 provide that steps be taken before the instruments are placed in the sterilizer, that is, in a preferred procedure, the instruments to be sterilized are first washed and then immersed in a pre-conditioning solution, that is a pre-conditioning solution containing a wetting agent and a detergent or, alternatively, they may be placed in a humidifier at 100% RH and 50° C. for at least two hours.

Returning once again to the aforementioned DIN test piece, dipping the heretofore described stoppered DIN test piece in a pre-conditioning solution as mentioned above would be ineffective, because the solution would not reach the inside of the test piece. On the other hand, dipping the unstoppered DIN test piece into a pre-conditioning solution causes the spore preparation to be washed out of the tube. Failing to unstopper the tube before exposure to 100% RH at 50° C. is equally inappropriate. Testing a gaseous sterilization system which operates at atmospheric pressure, which is not equipped with vacuum and pressure pumps, and which, therefore, requires that all obstructions to the free circulation of gas be removed before sterilization, with a tightly stoppered glass test tube is unrealistically severe.

Accordingly, it is an object of the present invention to provide an apparatus and method for efficaciously testing the sufficiency of sterilization and which avoids the possibility of chance bacterial contamination of the bacterial spore disc test piece after exposure to the sterilant.

Another object of the invention is to provide an apparatus and method for testing the sufficiency of sterilization for use with a sterilization system in which a pre-conditioning solution may be used prior to the actual step of sterilization.

Another object of the invention is to provide an apparatus and method for determining the presence or absence of live microorganisms, bacteria or the like, following sterilization in a sterilization apparatus in an efficient manner which is both time-saving and accurate and which eliminates the requirement for a high degree of skill and care.

A further object of the invention is to provide a reliable and convenient sterilizing test apparatus and method for use with known sterilization apparatus and methods, for example for use with a sterilization apparatus of the type set forth in the aforementioned U.S. Pat No. 3,476,506 and which is modeled after the aforementioned DIN Committee Blood Suspended Bacterial Spore Challenge but, unlike that test piece, is designed to test the entire sterilization process, including the preparation, the preconditioning and the packaging of the instruments as well as the adequacy of exposure to the sterilization.

Another object of the invention is to provide a reliable and convenient sterilizing test apparatus and method for use with sterilization systems such as that disclosed in U.S. Pat. No. 4,276,263 issued June 30, 1981 and which is assigned to the present assignee H. W. Andersen Products Inc. of Oyster Bay, N.Y.

Other features which are considered characteristic of the invention are set forth in the appended claims.

Although the invention is illustrated and described in relationship to specific embodiments, it is nevertheless not intended to be limited to the details shown, since various modifications and structural changes may be made therein without departing from the spirit of the invention and within the scope and range of equivalents of the claims.

The construction and operation of the invention, however, together with additional objects and advantages thereof will be best understood from the following description of specific embodiments when read in connection with the accompanying drawings.

SUMMARY OF THE INVENTION

The aforesaid objects are attained by providing a test tube in which a bacterial spore element is disposed and placing a sealed glass ampule containing a sterile liquid culture medium in the test tube. A plunger is fitted slidingly in the open end of the test tube above the ampule, the plunger having a fenestration closed with a hydrophobic filter element. In use, the apparatus is exposed to sterilization, and thereafter the plunger is pushed down into the test tube to engage the ampule to slide the latter into engagement with an ampule-engaging means to thereby fracture or break the ampule so that the contents of the ampule are released into the test tube to contact the spore element, whereby the apparatus is then subjected to incubation, the sufficiency of the sterilization being thereby determined.

DESCRIPTION OF THE PREFERRED EMBODIMENTS

Figure 1:
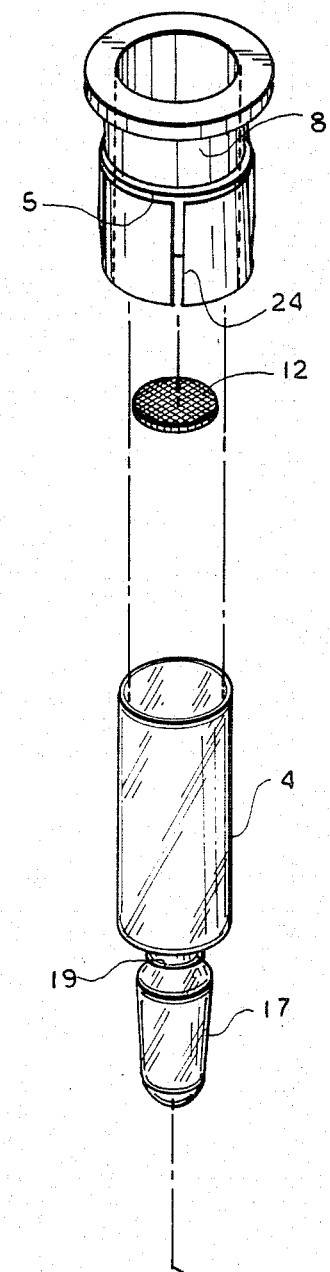
FIG. 1 is an exploded view of a testing apparatus according to one embodiment of the invention.
Figure 1:
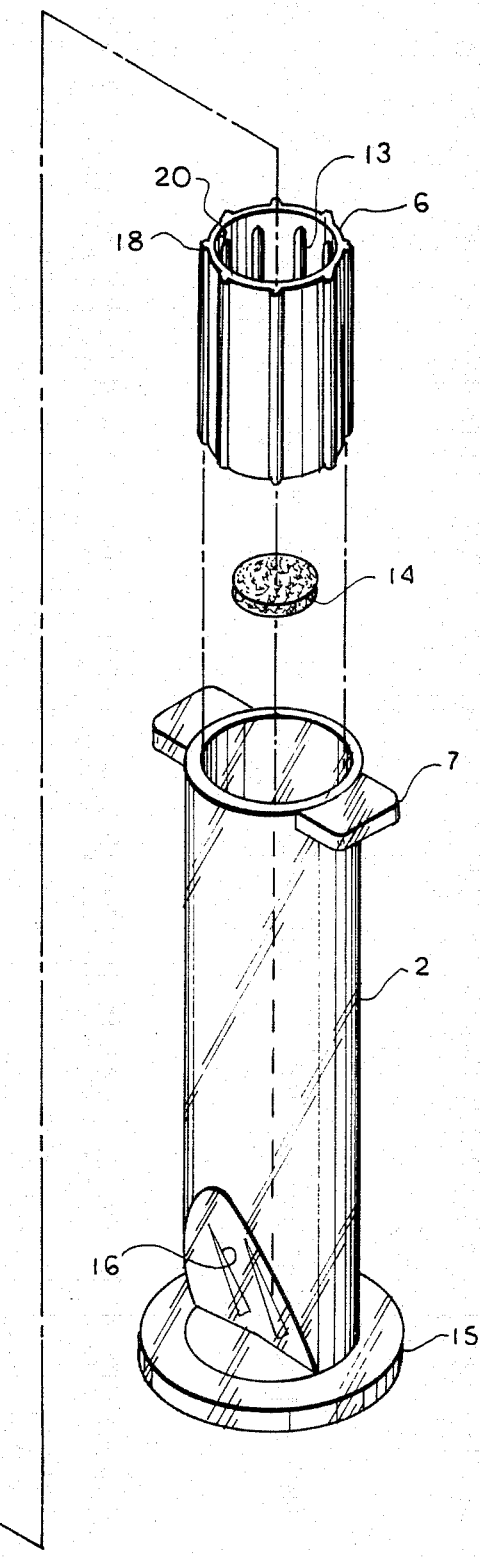
Figure 2:
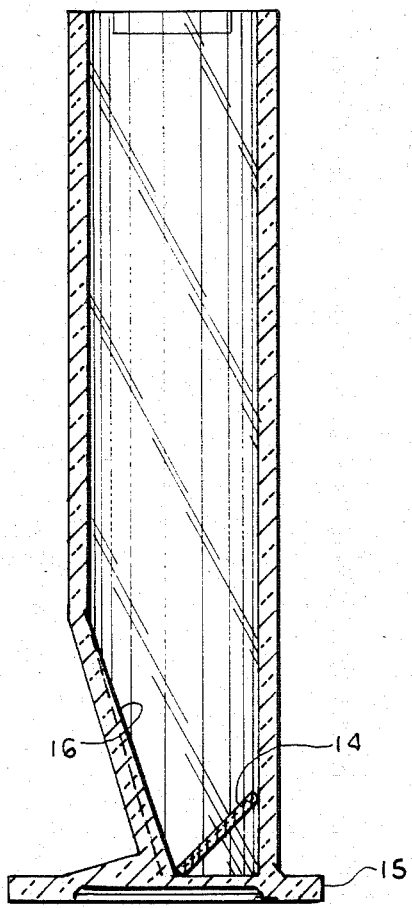
FIG. 2 is a sectional view of the test tube taken along a vertical bisecting plane.

Referring to the drawings, there is shown a clear, virtually unbreakable, especially shaped plastic test tube 2 which is adapted to receive a closed glass ampule 4 of sterile cultural broth. A grooved plastic ampule holder 6 is disposed around the ampule 4 and fits into the plastic test tube 2. A plunger 8 is also adapted to fit within the plastic test tube and is provided with a fenestration 10 closed with a hydrophobic filter element such as a disc 12. A bacterial spore element such as a disc 14 containing, for example, about 1,000,000 *Bacillus subtilis* variant *niger* (*B. globigii*) spores suspended in sheep's blood and dessicated at 50° C. is disposed in the test tube 2.

The test tube 2 is preferably made of a strong, clear, and rigid plastic, for example, polycarbonate or crystal polystyrene. The ampule holder 6 and plunger 8 may be made of a plastic material, for example, polyethylene or polypropylene. The hydrophobic filter 12 may be of the supported membrane type, using an acrylic copolymer filter matrix of less than 1 $\mu$m pore size, for example, sold by Gelman Manufacturing Co. of Ann Arbor, Mich., as ACROPORE, or as sold by Pall Manufacturing Co. of Glen Cove, N.Y., as EMFAB-TV.

Figure 8:
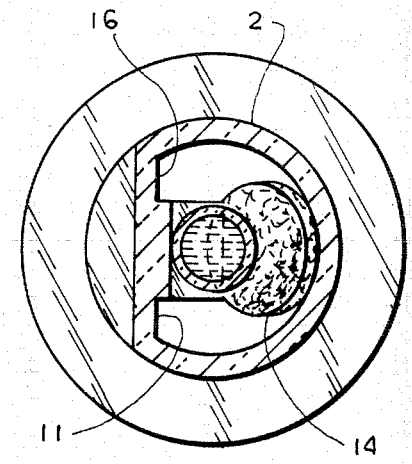

The test tube 2 has a base 15 to support it in an upright position. Its distal end is wedge-shaped as indicated at 16 to allow the ampule of culture broth to be easily broken open by merely pressing on the plunger 8 in the mouth of the tube 2. Thus it will be seen that the plunger 8 may be manually pushed into the test tube 2 with the aid of lateral projections 7 such that the end of the plunger 8 engages the ampule and pushes the latter against the wedge 16 to thereby snap off the neck 17 of the ampule at its score line 19. The wedge 16 may have a slightly raised portion 11 (FIG. 8) against which the ampule is pushed by the plunger 8. When the neck of the ampule breaks off, the contents of culture broth spill into the test tube and thereby allows the culture to be made without taking any chance of inadvertent contamination of the culture broth during transfer of the spore preparation.

Figure 3:
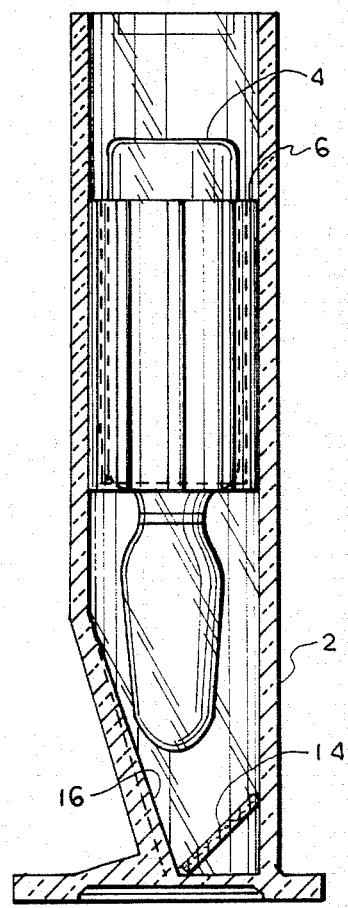
FIG. 3 is a view similar to FIG. 2 but also showing the ampule and the ampule holder around the ampule.

The ampule holder has ridges 18 defining boundaries of channels or grooves 20. Thus the grooves 20 provide communication between the open end of the test tube and the distal end. The unit is shipped with the ampule 4 and the ampule holder 6 in the test tube 2, for example as shown in FIG. 3, so that the ampule holder cushions and protects the glass ampule during shipment. The grooved ampule holder 6 also allows a gaseous or liquid sterilant to pass through the open end of the test tube to the distal end where the spore disc 14 is located. The ampule holder also allows a pre-conditioning solution containing a wetting agent and a detergent to reach the spore disc 14 when the unit is immersed in such a pre-conditioning fluid as will be described hereinafter. The grooved ampule holder 6 also directs the top of the ampule against the opening wedge 16 when the culture is finally to be made. The inside of the ampule holder 6 may also have longitudinally extending ridges 13.

The ampule holder 6 has an inner diameter to snugly accommodate and receive the ampule 4 and the plurality of longitudinal ridges 18 on the outside of the ampule holder circumscribe a diameter corresponding to the inner diameter of the test tube 2 to thereby snugly accommodate and guide the ampule holder 6 in the test tube 2.

Figure 4:
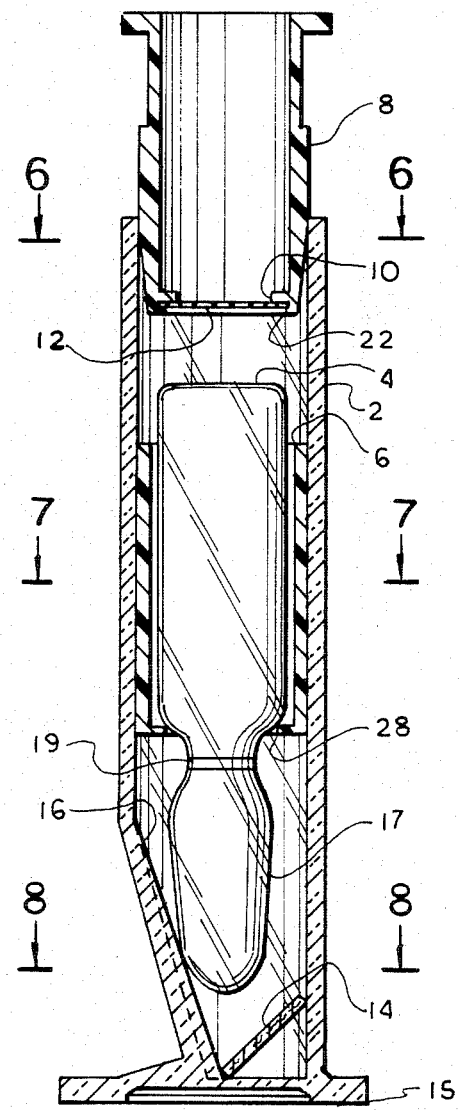
FIG. 4 is a sectional view of the unit shown in FIG. 1 but in an assembled position and taken along a vertical bisecting plane.

In addition, the ampule holder 6 has a slight inner flange 28 (FIG. 4) portion which engages the ampule 4 so that when the ampule 4 is pushed downwardly by the plunger 8, the ampule holder 6 is also pushed down due to such engagement.

Figure 6:
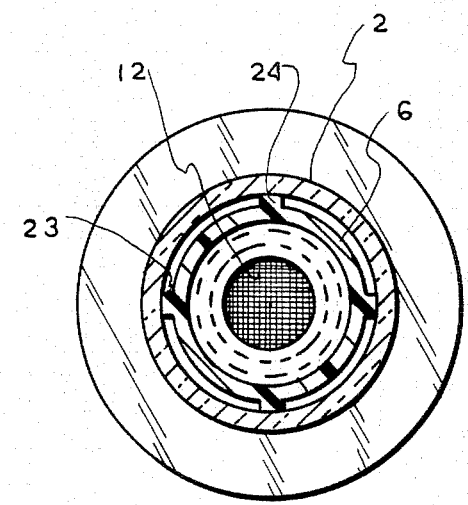
FIGS. 6, 7 and 8 are sectional views taken respectively along the cutting planes VI—VI, VII—VII, and VIII—VIII in FIG. 4.
Figure 5:
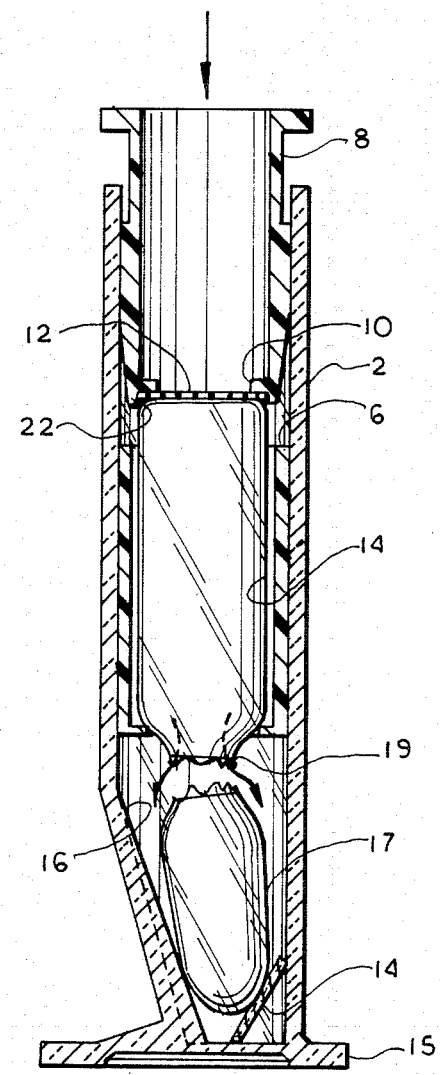
FIG. 5 is a view similar to FIG. 4 but showing a different operating position wherein the plunger has pushed the ampule into the test tube and the neck of the ampule has broken off.
Figure 7:
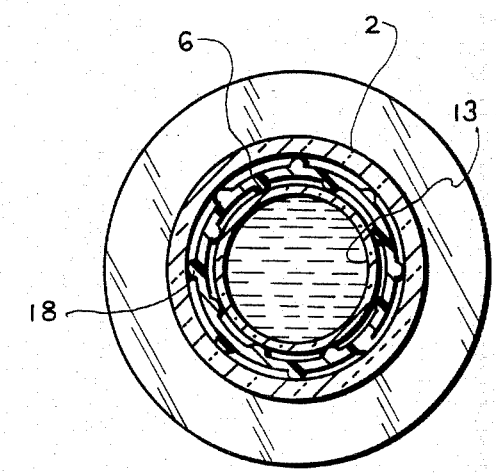

The plunger aperture 10 is closed by the hydrophobic filter 12. The filter 12 is placed in a recess in the end of the plunger over the opening 10 and secured in place by a closure ring 22 which may be secured by adhesive, heat sealing, mechanical pressure or the like. In this regard, FIG. 1 is an exploded view and that although the filter 12 and ring 22 are shown separately in the left-hand half of FIG. 1, the plunger 8 is manufactured with the filter 12 and ring 22 in place forming the self-contained plunger 8. The plunger 8 may have a plurality of longitudinally extended ridges 24 which engage the inside wall of the test tube 2 to snugly fit and guide the plunger as it is inserted in the test tube. The plunger is hollow as clearly shown in the upper portion of FIG. 4 and has one or more rings 5 which fit snugly into the test tube and provide a sealing element between the test tube 2 and plunger 8 when the plunger is inserted into the test tube as shown in FIG. 5. Passageways 23 (FIG. 6) are formed between the ridges 24.

Figure 4A:
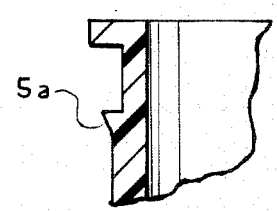
FIG. 4a is a partial sectional view of an alternate embodiment.

The ring 5 may have an outer diameter equal to or just slightly greater than the inner diameter of the test tube 2 so that in the latter case, ring 5 has to be slightly compressed to fit into the test tube 2 to thereby provide a snug sealing fit against the inside wall of the test tube 2. Also the ring may have a conical portion as shown at 5a in the alternate embodiment in FIG. 4A.

At the end of the sterilization cycle, the plunger 8 is used both as a means to break the ampule of culture broth aseptically and as a stopper for the culture tube that is both hydrophobic and allows oxygen to reach the growing organisms thereby speeding the development of a positive test.

When the plunger 8 is in place inserted in the test tube 2, for example as shown in FIG. 5, the plunger 8 including the filter 12 serves to retain liquid in the test tube 2 in the event the latter is inadvertently tipped over. Also the filter 12 allows air to pass into the test tube 2 while preventing random bacteria from entering the test tube 2 which could otherwise result in a false positive test result.

The sealed glass ampule 4 may suitably contain, for example, 5 ml. of sterile nutrient broth with added dextrose and a pH indicator. *Bacillus subtilis* variant *niger* (*B. globigii*) grows readily in this broth producing cloudiness after 24 hours of incubation and a color change from magenta to yellow with an orange pigmented layer of surface growth after 48 hours of incubation at 37° C. The same growth characteristics are observed at room temperature (20° C.–30° C.) after significantly longer incubation periods.

When it is required to include a pre-conditioning procedure in the sterilization process, the test tube 2 and its contents are dipped in a pre-conditioning solution containing a wetting agent and a detergent and then are placed on a paper towel to drain dry. The test tube 2 may be dipped in the pre-conditioning solution with the plunger 8 partially inserted in the test tube, that is inserted partially to a position in which the sealing ring 5 does not engage the test tube 2 so that the pre-conditioning solution will pass into the test tube through the passages 23 between the ridges 24. The test tube 2 with the partially inserted plunger 8 are then wrapped in conventional cloth or the like wrappings. The wrapped test tube 2 and partially inserted plunger 8 are then placed in the sterilization unit, suitably at the most inaccessible point for sterilizing gas to reach within the load to be sterilized.

Alternatively, the test tube 2 with its contents and the plunger 8 not inserted in the test tube may be separately dipped in the pre-conditioning solution and separately wrapped in the wrappings before being placed in the sterilization unit.

An example of a wetting agent is "AMMONYX LO" sold by Onyx Chemical Co., Division of Millmaster Onyx Corp. of Jersey City, N.J., and which is set forth in U.S. Pat. No. 3,296,145.

When the sterilization cycle is finished, the culture is made by opening the wrappings in which the test tube 2 and plunger 8 were wrapped, and breaking the ampule and simultaneously sealing the test tube by pushing the plunger 8 down against the test tube wedge 16. The test tube is thus sealed by the inserted plunger 8 and its sealing ring 5 and is then placed in an incubator in an upright position on its base 15 so that the broth covers the paper spore element 14. The unit is observed after 24 and 48 hours of incubation at 37° C.

A positive culture is easily recognized through the transparent test tube 2 after 48 hours incubation by a color change of the broth from magenta to yellow, and the typical orange layer of surface of growth in the pouch. At 24 hours incubation, although this surface layer may or may not be present, a definite cloudiness of the broth usually occurs along with a color change of the broth from magenta to yellow. If the broth remains magenta after 48 hours of incubation, the spores were killed, indicating that the load in the sterilizing unit was exposed to conditions prior to and during the sterilizing cycle adequate to assure sterilization.

This test apparatus and method were conceived to allow those unskilled in bacteriological techniques to perform an accurate cultural test for sterility. In this miniature laboratory, the simple mechanical breaking of the ampule 4 replaces the laboratory procedure of aseptically removing the spore element from its wrappings and placing it in a flamed tube of culture medium. The culturing procedure is performed in the equivalent of a sterile chamber. This easily-handled, compact control unit provides the materials necessary for assuring that the entire load in a sterilizing unit was exposed to conditions adequate for sterilization.

The bacteria, spores, or microorganisms employed may be of the type well known in sterilization tests. These may be, for example, *Bacillus subtilis, Clostridium sporogenes,* or *Bacillus sterothermophilus.* Many other species and variants can be used. Merely by way of example, the following design characteristics have been found to provide satisfactory test results: an ampule of ten cubic centimeters capacity containing approximately seven or eight cubic centimeters of culture medium in the form of, e.g., Fluid Thioglycollate.

From the above, it will be seen that because of the ampule 4 and ampule holder 6 fit snugly in the test tube 2, that these elements may be inserted in the test tube prior to shipment so that they are retained in position in the test tube and thereby prevent the spore disc 14 from coming out or otherwise being lost. Also the entire apparatus may be vacuum sealed in a package made of metal foil or the like. Accordingly, when the user is ready to use the unit, the vacuum-tight packaging is removed and the user is assured that the spore disc is of standard hydration at use. Loss of a vacuum-tight appearance indicates a hole in the package and the possibility that the spores contained therein are either over or under hydrated.

It will be further noted that during the immersion in the pre-conditioning solution, the liquid can enter the test tube through the longitudinal grooves 20 in the ampule holder. Since the sheep's blood suspended bacterial spores are absorbed into a filtered paper disc 14, they cannot be washed out of the test tube when thus immersed in the pre-conditioning solution. Also since the spore disc 14 is packaged at the bottom of the test tube 2 with a sterile ampule of appropriate culture medium securely suspended over it, further assurance is thereby provided that the spore disc 14 will not be accidentally lost from the test apparatus.

After the unit is subjected to the sterilization atmosphere and the plunger is inserted in the test tube to break the ampule, the plunger thereby seals the test tube, the seal being effected by the ring 5 as previousely described. Accordingly, with the test tube sealed, if the test tube is inadvertently tipped over, the liquid contents will not spill out because the filter 12 will not permit the liquid to pass through. In addition, the filter 12 will prevent random bacteria from entering into the test tube. The filter 12 also allows oxygen to reach the growing organisms thereby speeding the development of a positive test.

Figure 9:
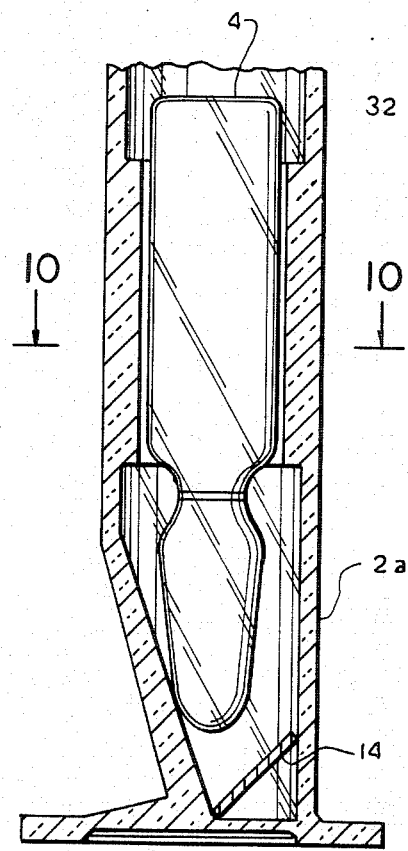
FIG. 9 is a partial sectional view taken along a vertical bisecting plane of an alternate embodiment.

FIG. 9 shows an alternate embodiment wherein a portion of the longitudinal length of the test tube 2a is integrally provided with a plurality of longitudinal ribs 30, the inner diameter of the plurality of the ribs 30 being such as to snugly receive and accommodate the ampule 4. With this embodiment, the need for a separate ampule holder, such as the ampule holder 6 in the embodiment of FIG. 1, is eliminated. Passageways 32 between the ribs 30 provide for access of the fluids or gases past the test tube to the spore disc 14.

Figure 11:
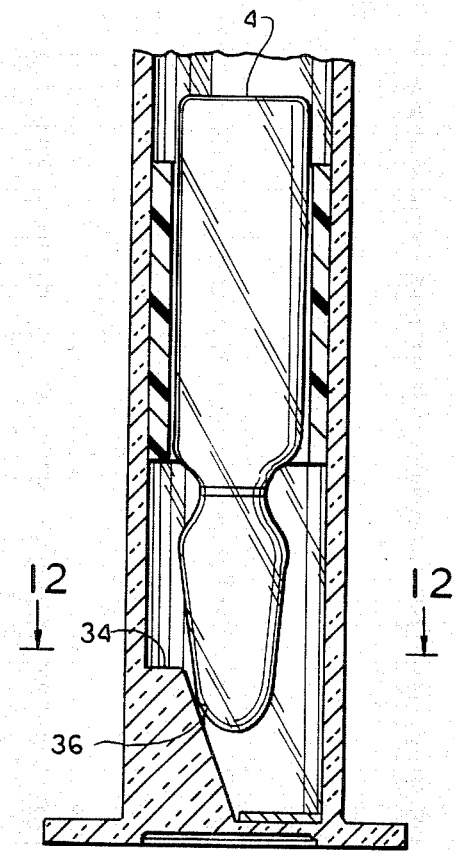
FIG. 11 is a sectional view taken along a vertical bisecting plane of another alternate embodiment.
Figure 10:
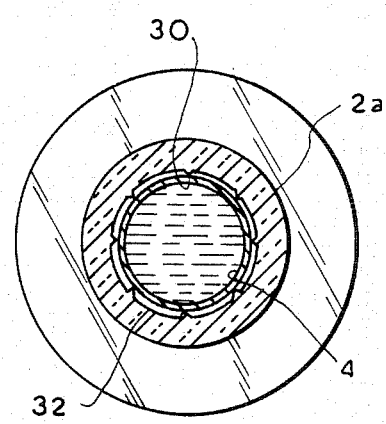
FIG. 10 is a sectional view taken along the cutting plane X—X in FIG. 9.
Figure 12:
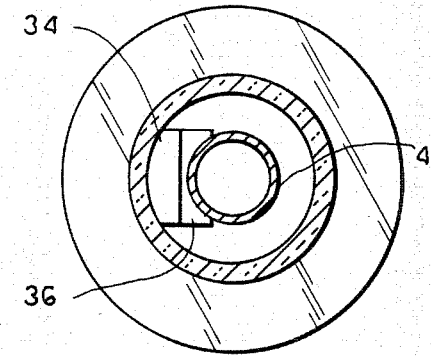
FIG. 12 is a sectional view taken along the cutting plane XII—XII in FIG. 11.

FIG. 11 shows a further alternative embodiment wherein the wedge-shaped construction of the FIG. 1 embodiment is replaced by a lateral protrusion 34 having a slanted end portion 36 for engaging the ampule 4 to break the latter as the plunger pushes in the ampule 4 as previously described.

Although reference has heretofore been made to utilizing the invention in conjunction with gaseous and liquid sterilants, the invention may be utilized to test the sufficiency of any type of sterilization including, but not limited to, exposure to heat whether it be wet or dry and including steam, exposure to gaseous sterilants such as ethylene oxide, propylene oxide, methylene bromide and other gases including mixtures thereof, exposure to liquid sterilants such as chlorine, phenol or iodine based sterilants and other liquids including mixtures thereof, and exposure to radiation and other sterilization such as X-rays.

What is claimed is:

1. Apparatus for testing the sufficiency of sterilization comprising a test tube having an open end and a closed distal end, said test tube being adapted to receive a bacterial spore element, a sealed ampule containing a sterile liquid culture medium, said ampule being disposed in said test tube, engaging-breaking means in said test tube, and a hollow open-ended plunger fitted slidingly into the open end of said test tube into a position where said plunger is retained in said test tube and said ampule is disposed in said test tube in an unbroken state, said plunger having sealing means operable to seal off communication between the outside of said plunger and the inside of said test tube, a hydrophobic filter element sealing the distal fenestration of said plunger and allowing passage of air in and out of said test tube, said plunger being constructed and disposed such that upon increased insertion of the plunger into said test tube, said plunger engages said ampule to slide the latter into engagement with said engaging-breaking means in said test tube to thereby fracture or break the ampule so that its contents are released into said test tube to contact said spore element, said filter allowing oxygen to pass into said test tube while preventing bacteria from entering into said test tube, said filter also retaining the liquid in said test tube.

2. Apparatus according to claim 1 wherein said spore element is disposed in said distal end of said test tube, said spore element and said ampule being disposed in said test tube such that during shipment of the apparatus, said spore element is retained in the distal end of the test tube.

3. Apparatus for testing the sufficiency of sterilization comprising a test tube, said test tube being adapted to receive a bacterial spore element, a sealed ampule containing a sterile liquid culture medium, retaining means on the inside of said test tube for snugly and slidably retaining said ampule in said test tube, engaging-breaking means in said test tube, and a hollow open-ended plunger fitted slidingly into the open end of said test tube, said plunger having rib means providing communication between the inside and outside of said test tube and sealing ring means sealing off said communication, said plunger being insertable into said test tube into a position where said plunger is retained in said test tube and said ampule is disposed in said test tube in an unbroken state, a hydrophobic filter element sealing the distal fenestration of said plunger and allowing passage of air in and out of said test tube, said plunger being constructed and disposed such that upon insertion of said plunger into said test tube, said plunger engages said ampule to slide the latter into engagement with said engaging-breaking means to thereby break the ampule so that its contents are released into said test tube to contact said spore element, said filter allowing oxygen to pass into said test tube while preventing bacteria from entering into said test tube, said filter also retaining the liquid in said test tube.

4. Apparatus according to claim 3 wherein said test tube has a base element at its distal end for supporting the test tube in an upright position.

5. Apparatus according to claim 3 wherein said retaining means is an ampule holder having a plurality of longitudinal extending external ridge elements which are adapted to engage the inside walls of said test tube, whereby when the ampule holder is inserted in the test tube, longitudinal extending passages are provided between the ridge elements and between the outer wall of the ampule holder and the inner wall of the test tube.

6. Apparatus according to claim 5 wherein said ampule holder has a plurality of longitudinal extending ridges along the inside wall thereof.

7. Apparatus according to claim 5 wherein said ampule holder has an internal ring at one longitudinal end thereof, said ring having an inner diameter less than the outer diameter of said ampule such that when the ampule is pushed into the test tube by said plunger, said ampule engages said ring and causes the ampule holder to move simultaneously with the ampule as the latter is pushed into the test tube by said plunger.

8. Apparatus according to claim 3 wherein said retaining means comprises a plurality of longitudinally extending ridge elements integrally formed on the inside of said test tube, said ridge elements being adapted to engage said ampule such that when the ampule is inserted into the test tube, longitudinal extending passages are provided between said ridge elements.

9. Apparatus according to claim 3 wherein said engaging-breaking means comprises a wedge-shaped generally flat wall, said flat wall being disposed at an acute angle relative to the center line of said test tube.

10. Apparatus according to claim 9 wherein said generally flat wall has a raised portion against which the end portion of the ampule is forced when the ampule is pushed into the test tube by said plunger.

11. Apparatus according to claim 3 wherein said engaging-breaking means comprises a protrusion extending inwardly into said test tube.

12. Apparatus according to claim 3 wherein said plunger is generally hollow, said hydrophobic filter element being in the form of a disc, and a ring element secured to said plunger for retaining said hydrophobic filter in place on said plunger.

13. Apparatus according to claim 3 wherein said sealing ring means comprises a sealing ring on said plunger for sealingly engaging the inside wall of said test tube.

14. Apparatus according to claim 13 wherein said sealing ring has a diameter greater than the inner diameter of said test tube, said sealing ring being made of a material sufficiently resilient so as to be compressed to a diameter equal to the inner diameter of said test tube as the plunger is pushed into said test tube.

15. Apparatus according to claim 14 wherein said sealing ring is integral with said plunger.

16. Apparatus according to claim 13 wherein said sealing ring has at least a partial conical configuration.

17. A method of testing the sufficiency of sterilization comprising the steps of providing a sterile liquid culture medium and a source of microorganisms, containing said source of microorganisms in a test tube, containing said medium in a sealed ampule mounted slidably in said test tube, providing a hollow open-ended plunger for said test tube which fits slidably in said test tube and which has a fenestration closed with a hydrophobic filter which allows air to pass therethrough, exposing said apparatus including said source of microorganisms to a sterilant, manually forcing said plunger down into said test tube so that said ampule is broken and said medium contacts said source of microorganisms, placing the test tube in an incubator to effect incubation to ascertain whether a positive culture is obtained, admitting air into said test tube through said hollow open-ended plunger and said hydrophobic filter to allow the oxygen in the air to reach the growing organisms in the test tube during said incubation, said hydrophobic filter preventing random bacteria from entering the test tube during incubation, and said hydrophobic filter also precluding liquid from spilling from said test tube should said test tube be inadvertently tipped over during incubation.

18. A method according to claim 17 comprising providing said test tube in the form of a clear rigid plastic so that color change of the contents therein may be readily observed.

19. A method according to claim 17 wherein said test tube with the source of microorganisms and the ampule holder and the plunger are exposed to the sterilant as a unit, whereby during exposure to said sterilant, sterilant passes into the test tube along longitudinal grooves between the plunger and the test tube and between the ampule and the test tube.

20. A method according to claim 17 wherein said test tube with said source of microorganisms and the ampule are subjected to a liquid pre-conditioning solution prior to exposure to said sterilant, whereby the liquid solution passes into the test tube through longitudinal passages formed between the ampule and the inside wall of the test tube such that the test tube, ampule and the source of microorganisms are thereby exposed to the liquid pre-conditioning solution as a unit and misplacement of the source of microorganisms is precluded inasmuch as said source of microorganisms is retained in the distal end of the test tube and prevented from coming out by the ampule disposed in the test tube above said source of microorganisms.

21. A method according to claim 17 wherein said test tube has a distal end, further comprising disposing said source of microorganisms in said distal end of said test tube, and disposing said ampule in said test tube to thereby retain said source of microorganisms in said distal end of the test tube and utilizing said test tube to protect said ampule during shipment prior to use.

* * * * *